US011026875B2

(12) United States Patent
Auriol et al.

(10) Patent No.: US 11,026,875 B2
(45) Date of Patent: Jun. 8, 2021

(54) SKIN RESTORATION PRODUCT

(71) Applicant: Givaudan SA, Vernier (CH)

(72) Inventors: Daniel Auriol, Roques sur Garonne (FR); Hanane Chajra, Tournefeuille (FR); Fabrice Lefevre, Auterive (FR)

(73) Assignee: Givaudan S.A., Vernier (CH)

( * ) Notice: Subject to any disclaimer, the term of this patent is extended or adjusted under 35 U.S.C. 154(b) by 234 days.

(21) Appl. No.: 16/089,524

(22) PCT Filed: Apr. 10, 2017

(86) PCT No.: PCT/EP2017/058516
§ 371 (c)(1),
(2) Date: Sep. 28, 2018

(87) PCT Pub. No.: WO2017/178415
PCT Pub. Date: Oct. 19, 2017

(65) Prior Publication Data

US 2020/0297611 A1 Sep. 24, 2020

(30) Foreign Application Priority Data

Apr. 11, 2016 (EP) .................................... 16290066

(51) Int. Cl.
*A61K 8/60* (2006.01)
*A61K 8/23* (2006.01)
*A61Q 19/08* (2006.01)

(52) U.S. Cl.
CPC ................ *A61K 8/602* (2013.01); *A61K 8/23* (2013.01); *A61K 8/60* (2013.01); *A61Q 19/08* (2013.01)

(58) Field of Classification Search
CPC ............ A61K 8/602; A61K 8/23; A61K 8/60
See application file for complete search history.

(56) References Cited

U.S. PATENT DOCUMENTS

2013/0012475 A1* 1/2013 Auriol .................... A61P 27/02 514/62

FOREIGN PATENT DOCUMENTS

| | | | |
|---|---|---|---|
| EP | 2072032 | A1 | 6/2009 |
| JP | 2014088329 | A | 5/2014 |
| WO | WO 2014/091980 | A1 | 6/2014 |

OTHER PUBLICATIONS

International Search Report for PCT/EP2017/058516 dated May 22, 2017.
International Written Opinion for PCT/EP2017/058516 dated May 22, 2017.

* cited by examiner

*Primary Examiner* — Pancham Bakshi
(74) *Attorney, Agent, or Firm* — Curatolo Sidoti Co., LPA; Salvatore A. Sidoti; Floyd Trillis, III

(57) ABSTRACT

A composition comprising N-acetyl-glucosamine-6-phosphate, glucuronic acid, and a magnesium sulfate in the proportions of 50 to 75, 55 to 83 and 33 to 66 mmoles/kg respectively. The composition has restorative effects on aged and wrinkled skin.

6 Claims, 6 Drawing Sheets

Untreated condition

Active ingredient at 0.5 mM

Placebo

Composition at 2%

Cheek baby skin

SKIN RESTORATION PRODUCT

CROSS REFERENCE TO RELATED APPLICATIONS

This application is a national stage application of International Application No. PCT/EP2017/058516, filed 10 Apr. 2017, which claims priority from European Patent Application No. 16290066.6, filed 11 Apr., 2016, which applications are incorporated herein by reference.

This disclosure relates to skin tightening and to compositions and methods for achieving this.

Skin is composed of three layers, the epidermis at the surface, and under that the dermis and then the hypodermis. Wrinkling and sagging with age is mainly a result of changes in the dermis. The dermis consists of cells held in an extracellular matrix composed of glycosaminoglycans (sulfated and unsulfated), such as chondroitin sulfate, heparan sulfate, dermatan sulfate and hyaluronic acid, proteins (e.g. collagens and elastin), hybrid protein-sugar molecules and proteoglycans. In young skin, the extracellular matrix is dense and compact, but as the person ages, some of the dermis constituents, particularly the glycosaminoglycans and the proteoglycans, diminish, leading to the epidermis noticeably wrinkling and sagging, loss of firmness and elasticity.

The universality of the problem is evidenced by the number of alleged remedies available, ranging from plastic surgery to injection of botulinum toxin.

It has now been found that aged skin can be at least partially restored by the application of a particular composition. There is therefore provided a composition comprising N-acetyl-glucosamine-6-phosphate, glucuronic acid, and a magnesium sulfate in the proportions of 50 to 75, 55 to 83 and 33 to 66 mmoles/kg respectively.

There is further provided a skin restoration product comprising a composition as hereinabove defined.

There is further provided a method of restoring aged skin, comprising the topical application of a product as hereinabove defined.

The three components are all commercially available. The N-acetyl-glucosamine-6-phosphate and glucuronic acid may be used in the form of their alkali metal (usually sodium) salts.

Magnesium sulfate may be used in any of its commercially available forms, anhydrous or the $7H_2O$ hydrated form (Epsom salts).

In a particular embodiment, the three components are in approximately equimolar proportions.

The composition hereinabove described provides a filling and lifting effect, thus diminishing and sometimes even removing completely sagging and wrinkling. It also improves the mechanical properties of the skin. It is believed, without limiting the disclosure in any way, that the composition acts to promote restructuring of the dermis components, such as collagen and elastic fibres, and a regeneration of the glycosaminoglycans and the proteoglycans missing from aged skin.

The composition may be incorporated in a skin restoration product, typically in a proportion of from 0.005-5% by weight. The skin restoration product will additionally contain those common ingredients used in the formulation of such compositions. These will depend on the nature of the composition, which may be fluid pastes, either aqueous or non-aqueous, or emulsions (W/O or O/W). Typical ingredients include glycols, oils, triglycerides, waxes, colouring matters and dyestuffs, emulsifiers, fragrances, preservatives, and the like. The product may be applied to the skin in the normal fashion of such products.

The disclosure is further described with reference to the following non-limiting examples.

Example 1

Preparation of a Skin Treatment Composition

For the preparation of a skin treatment composition, the raw materials were:

- Concentrated aqueous solution of N-acetyl-glucosamine 6-phosphate (concentration 440 mmoles/kg; pH lower than 2); prepared according to the method described in US patent publication 2013/00122475
- magnesium sulfate heptahydrate (246.47 Da); preparation M1880 (Sigma-Aldrich Chemie S.a.r.l., L'Isle d'Abeau Chesnes; 38297 Saint-Quentin Fallavier, France)
- sodium D-glucuronate, monohydrate (234.14 Da); preparation G8645 (Sigma-Aldrich) glycerin: preparation G7893 (Sigma-Aldrich)
- sodium hydroxide The preparation of 103 Kg of the composition was as follows:

6.695 moles of each compound were used. This meant 1.65 kg of magnesium sulfate heptahydrate (molecular mass 246.47) and 1.57 kg of sodium D-glucuronate monohydrate (molecular mass 234.14).

15.22 kg of concentrated and acidic N-acetyl-glucosamine 6-phosphate were introduced into the reactor. Agitation was started and the amount of water necessary to obtain a mass in the reactor of 35% of the final mass was added (20.83 kg). The magnesium sulfate was introduced into the reactor and agitation was maintained until complete dissolution, followed by the same procedure for the sodium D-glucuronate.

The pH of the solution was adjusted to a value ranging from 5.7 to 5.9 using a 2.0 N sodium hydroxide solution, and water then added to obtain a mass in the reactor corresponding to 51.5% of the final mass (for 103 kg, the final mass of the aqueous solution is 53 kg).

Glycerin was introduced into the reactor to obtain the final expected mass of the solution (50 kg added to 53 kg of aqueous solution). The final solution was filtered under sterile conditions (biosafety cabinet, sterile fitters and bottles) and stored at a temperature not exceeding 30° C.

Example 2

Effect of the Composition of Example 1 on Gene Expression of Enzymes Involved in Sulfated Glycosaminoglycan Synthesis Pathway Studied In Vitro on Normal Human Dermal Fibroblasts (45 Year-Old)

Study protocol: The composition was applied at 0.5 mM and 1 mM (i.e., each of N-acetyl-glucosamine-6-phosphate, sodium D-glucuronate, and magnesium sulfate were present at 0.5 or 1 mM) to normal human dermal fibroblasts NHDFs for 18 hours (n=3). TGF-β1 at 20 ng/mL was used as positive control. The extraction of the total RNAs was performed using the RNeasy™ Mini Kit. The reverse transcriptions (RTs) of the RNAs were then performed.

The results are shown in Table 1.

TABLE 1

Gene expression of enzymes involved in sulfated glycosaminoglycan synthesis pathway modified following normal human dermal fibroblasts treatment with the composition for 18 h.

| Gene identification | Relative gene expression RQ | P-Value | Concentration |
|---|---|---|---|
| carbohydrate (chondroitin 4) sulfotransferase 12 (CHST12) | 3.23 | 0.04 | 0.5 mM |
| carbohydrate (N-acetyl-galactosamine 4-sulfate 6-O) sulfotransferase 15 (CHST15) | 1.79 | 0.01 | 0.5 mM |
| chondroitin sulfate synthase 1 (CHSY1) | 1.76 | 0.05 | 0.5 mM |
| dermatan sulfate epimerase (DSE) | 1.57 | 0.00 | 0.5 mM |
| xylosylprotein beta 1,4-galactosyltransferase, polypeptide 7 (B4GALT7) | 1.51 | 0.01 | 0.5 mM |
| exostosin glycosyltransferase 1 (EXT1) | 1.33 | 0.02 | 0.5 mM |
| exostosin-like glycosyltransferase 2 (EXTL2) | 1.62 | 0.03 | 1 mM |
| beta-1,3-glycosyltransferase 3 (glucuronosyltransferase I) (B3GAT3)* | 1.60 | 0.02 | 1 mM |

RQ means relative gene expression in comparison to untreated cells (RQ > 1: increased gene expression − RQ < 1: decreased gene expression, and p values were mentioned to confirm the significance of the results).
*This enzyme was also over expressed at 0.5 mM but after 40 hours of cell treatment The composition significantly increased the gene expressions of enzymes involved in sulfated glycosaminoglycans synthesis pathway.

Example 3

Effect of the Composition on Gene Expression of Proteoglycans by Normal Human Dermal Fibroblasts (45 Year-Old)

Study protocol: The composition was applied at 0.5 mM and 1 mM to normal human dermal fibroblasts NHDFs for 18 hours (n=3). TGF-β1 at 20 ng/mL was used as positive control. The extraction of the total RNAs was performed using the RNeasy™ Mini Kit. The RTs of the RNAs were then performed. The results are shown in Table 2.

TABLE 2

Gene expression of proteoglycans modified following normal human dermal fibroblasts treatment with the composition for 18 h.

| Gene identification | Relative gene expression RQ | P-Value | Concentration |
|---|---|---|---|
| biglycan (BGN) | 1.81 and 1.71 | 0.04 | 0.5 mM and 1 mM |
| glypican 1 | 1.48 | 0.05 | 0.5 mM |

The composition significantly increased the gene expression of two proteoglycans, biglycan and glypican.

Example 4

Effect of Composition on Sulfated Glycosaminoglycans Synthesis In Vitro by Normal Human Dermal Fibroblasts (41 and 62-Year-Old)

Study protocol:

The composition was applied at 0.5 and 1 mM to normal human dermal fibroblasts (NHFs) over a period of 72 hours. Normal human fibroblasts (NHFs), were isolated from the skin dermis of 41 and 62-year-old Caucasian women donors (plastic surgery). Cells were seeded at 80 000 fibroblasts/well in 24-wells plates and were left to adhere for 24 hours at 37° C./5% $CO_2$ in complete DMEM (Dulbecco's Modified Eagle Medium) (with antibiotics and FBS, fetal bovine serum).

The cells were then treated with the composition in non-supplemented medium (without FBS) for 72 hours and incubated at 37° C./5% $CO_2$, and then total sGAG (sulfated Glycosaminoglycans) and HS (Heparan sulfate, or N-sulfated GAG) were dosed in culture supernatants and cells pellets (total proteins were dosed in cells pellets). Each product concentration was tested in duplicate. Furthermore, dosages were reported as a proportion of total amount of proteins. At the end of treatment, supernatants were collected. Cells were lysed in a papain containing buffer (Papaya latex Sigma P3125). Cells extracts were collected and centrifuged. Supernatants and cells pellets were dosed for sGAG, HS, or total proteins.

sGAG and HS dosage principles: Total sulfated GAG (sGAG), were dosed using the Blyscan™ sGAG Assay kit (Biocolor B1000 or B3000). The Blyscan™ assay is a quantitative dye-binding method for the analysis of sulfated proteoglycans and glycosaminoglycans (sGAG). The dye label used in the assay is 1,9-dimethylmethylene blue and the dye is employed under conditions that provide a specific label for the sulfated polysaccharide component of proteoglycans or the protein free sulfated glycosaminoglycan chains. The method consists of adding a specific blue dye reagent to an aliquot of supernatants or cells pellets which makes sGAG precipitate (a complex dye-sGAG is formed and precipitates out from the soluble unbound dye).

Centrifugation permitted the collection of a pellet of precipitate at the tube bottom. After having carefully drained the dye, the pellet was solubilized in a dissociation reagent (5-10% Sodium dodecyl sulphate). Absorbance was read at 656 nm in duplicate, in a 96-wells microplate. N-sulfated GAG was dosed indirectly, by dosing O-sulfated GAG and substracting it from the total sGAG, following a specific reaction. For this purpose, N-sGAG dosage was inhibited by a reaction with nitrous acid. After this reaction, O-sGAG level can be measured using the protocol as normal, and N-sulfated content was subsequently calculated from the difference between the total sGAG value (determined earlier) and the O-sGAG content.

Total proteins dosage principle: Total proteins dosage in cells pellets was performed in parallel by colorimetric method based on bicinchoninic acid (BCA). The principle of the BCA assay relies on the formation of a protein-$Cu^{2+}$ complex under alkaline conditions, followed by reduction of the $Cu^{2+}$ to $Cu^{+}$. BCA is highly specific for $Cu^{+}$ ion and forms a purple-blue complex with $Cu^{+}$ in alkaline environments, thus providing a basis to monitor the reduction of alkaline $Cu^{2+}$ by proteins. The amount of reduction and of BCA-$Cu^{+}$ complex is proportional to the protein concentration present and is quantified by spectrophotometric lecture at 570 nm. The dosage kit used was from Sigma (Sigma B9643). Standard range was prepared with BSA (Bovine Serum Albumin—Sigma A9418).

Results

Total sGAG (In Vitro Tests)

When results were totaled (cells pellets+supernatants), an induction of total sGAG by TGFβ treatment from fibroblasts was observed. This result validates the NsGAG experiment. The total sGAG synthesis with TGF beta was increased by 23% and 28% for the 41-year-old and the 62-year-old fibroblasts respectively, whereas it was increased by 28% and 16% with the composition, for the corresponding fibroblasts. (Table 3 and table 4).

TABLE 3

Evaluation of products effect on total sGAG synthesis (production + liberation) by 41 year-old fibroblasts treated for 72 h (data reported to total proteins amount).

| Condition tested | Total sGAG synthesis improvement | p-value |
|---|---|---|
| TGF beta : transforming growth factor beta | +23% | $p < 0.001$ |
| Composition at 1 mM | +34% | $p < 0.05$ |

TABLE 4

Evaluation of products effect on total sGAG synthesis (production + liberation) by 62 year-old fibroblasts treated for 72 h (data reported to total proteins amount).

| Condition tested | Total sGAG synthesis improvement | p-value |
|---|---|---|
| TGF beta: transforming growth factor beta | +28% | $p < 0.001$ |
| Composition at 1 mM | +16% | $p < 0.01$ |

NsGAG (In Vitro Tests)

When results were totalized (cells pellets+supernatants), an induction of N-sulfated GAG (heparin sulfate, HS) by TGFβ treatment from fibroblasts was observed. This result validates the NsGAG experiment. With TGFβ, the N-sulfated GAG synthesis was improved by +43% and +24% and with the composition by +66% and +32% at 1 mM, respectively for 41-year-old and 62-year-old donor (Table 5 and Table 6).

TABLE 5

Evaluation of the composition on total N sulfated GAG synthesis (production + liberation) by 41 year old fibroblasts treated for 72 h (data reported to total proteins amount).

| Condition tested | N-sulfated GAG synthesis improvement | p-value |
|---|---|---|
| TGF beta: transforming growth factor beta | +43% | $p < 0.001$ |
| Composition at 1 mM | +66% | $p < 0.05$ |

TABLE 6

Evaluation of the composition on total N sulfated GAG synthesis (production + liberation) by 62-year-old fibroblasts treated for 72 h (data reported to total proteins amount).

| Condition tested | N-sulfated GAG synthesis improvement | p-value |
|---|---|---|
| TGF beta: transforming growth factor beta | +24% | $p < 0.01$ |
| Composition at 1 mM | +32% | $p < 0.01$ |

Example 5

Effect of the Composition on Sulfated Glycosaminoglycans (Heparan Sulfate and Chondroitin Sulfate), Proteoglycans Synthesis and Dermis Organization Studied Using Normal Human Skin Explants (Maintained in Survival (41-Year-Old, Ex-Vivo Study)

Study protocol:

The composition was topically applied at 0.5 mM to normal human skin explants kept in survival on day 0 (D0), 1 (D1), 2 (D2), 5 (D5), 6 (D6), 7 (D7) and 8 (D8). The control explants did not receive any treatment except the renewal of the medium. Each condition was studied in triplicate.

For histological and immunohistological analysis, samples were either embedded in frozen condition or in paraffin. 5 to 7-μm-thick sections were made from these embedding samples for immunostaining analysis for heparin sulfate, chondroitin sulfate, decorin, perlecan and versican. Heparan sulfate immunostaining was realized on frozen sections with an anti-heparan sulfate monoclonal antibody (clone A7L6; Thermo, Ref: MA1-06821), diluted at 1:100 with water and revealed by FITC (SA 1001, Invitrogen). Chondroitin sulfate immunostaining was realized on paraffinized sections with an anti-chondroitin sulfate monoclonal antibody (clone CS-56; Abcam, Ref: ab11570) diluted at 1:400 with water and revealed by VIP (Vector, Ref. SK-4600). Perlecan immunostaining was realized on frozen sections with an anti-perlecan monoclonal antibody, (clone7B5; Invitrogen, Ref: 13-4400) diluted at 1:200 with water. Decorin immunostaining has been realized on frozen sections with an anti-decorin monoclonal antibody, (clone 9XX; Santa Cruz, Ref: sc-73896 diluted at 1:200 with water. Nuclei were post-stained with propidium iodide. The immunostainings were assessed by microscopical observation. The dermis organization of skin explants treated with the composition was assessed by biphoton microscopy to observe the organization of extracellular matrix components. An intense green color is linked to elastic fibers autofluorescence, whereas a blue color is linked to collagen fibers detection. The dermis ultrastructure was also assessed by transmission electron microscopy with a focus on collagen fibers, elastic fibers and telocytes (a cell type described as important in skin homeostasis and regeneration process) structures.

BRIEF DESCRIPTION OF DRAWINGS

The results are shown in the accompanying figures, whose details are given below.

Figure 1:
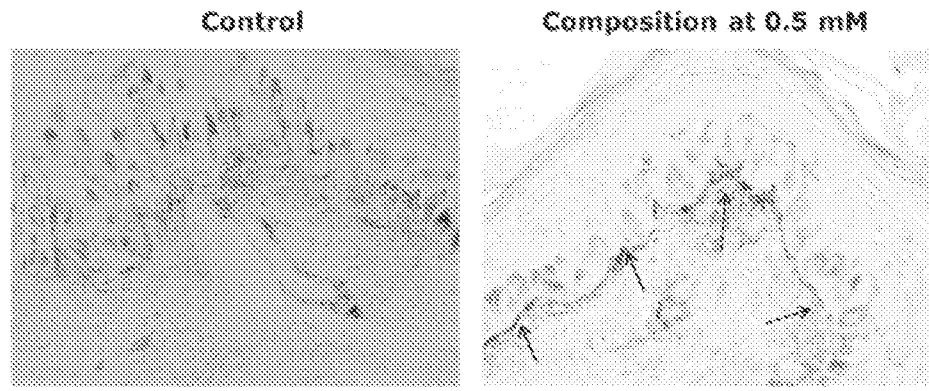
FIG. 1—effect of the composition on chondroitin sulfate. It was increased by 14% (arrows)
Figure 2:
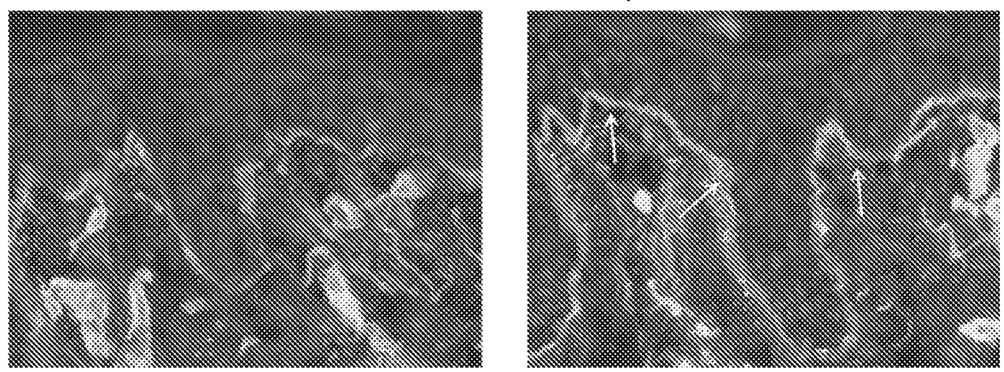
FIG. 2—effect of the composition on heparan sulfate. It was increased by 14% (white arrows)
Figure 3:
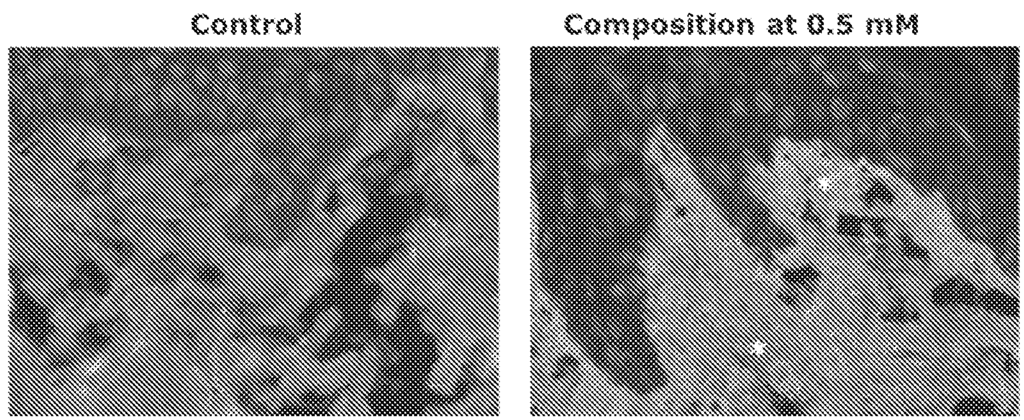
FIG. 3—effect of the composition on decorin. 18% increase observed (white asterisks)
Figure 4:
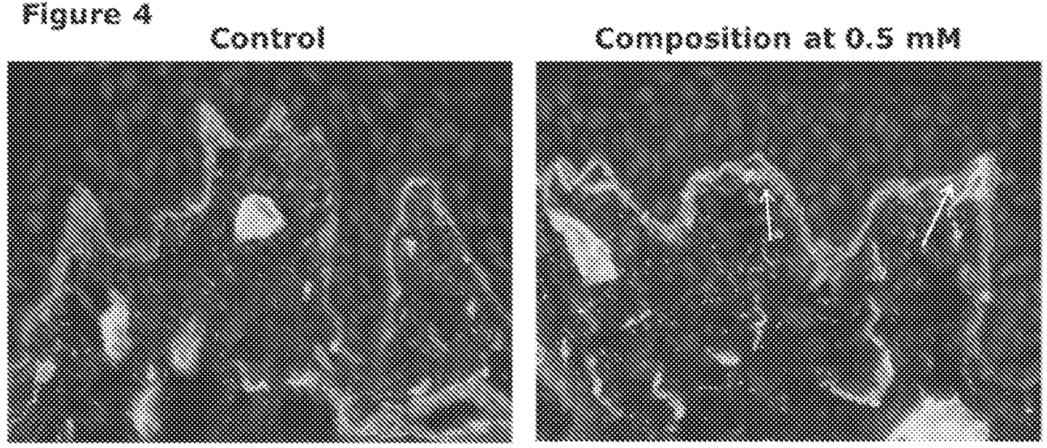
FIG. 4—effect of the composition on perlecan. 48% increase observed (white arrows)
Figure 5:
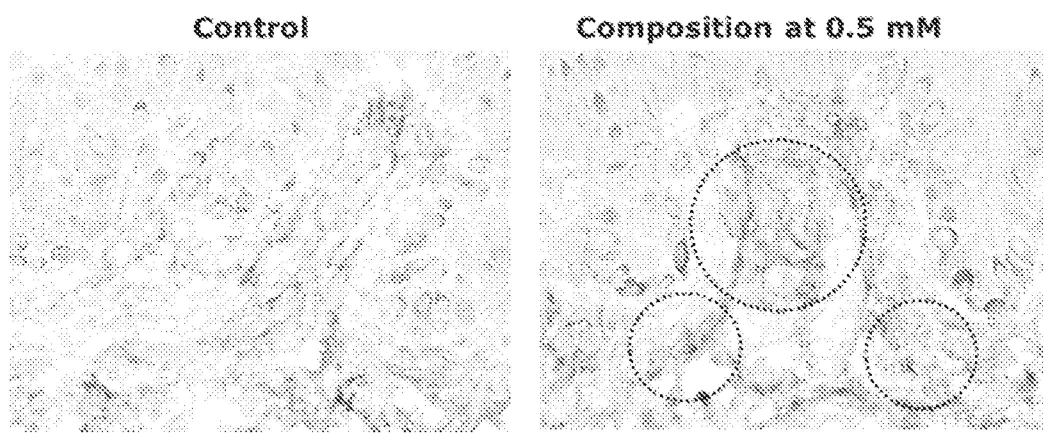
FIG. 5—effect of the composition on versican. The composition induces an increase in the versican expression (black dotted rings).
Figure 6:
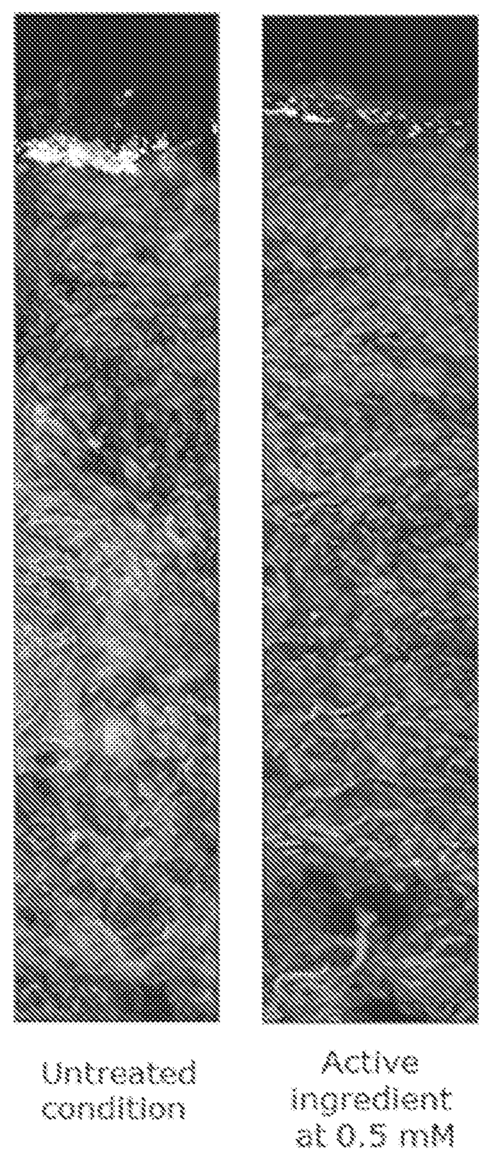
In FIG. 6, biphoton microscopy showed that the composition (at 0.5 mM) induced a visible effect on the skin fibers. Elastic fibers looked repaired end compacted, collagen fibers showed homogeneous diameters and a proper organization.
Figure 7:
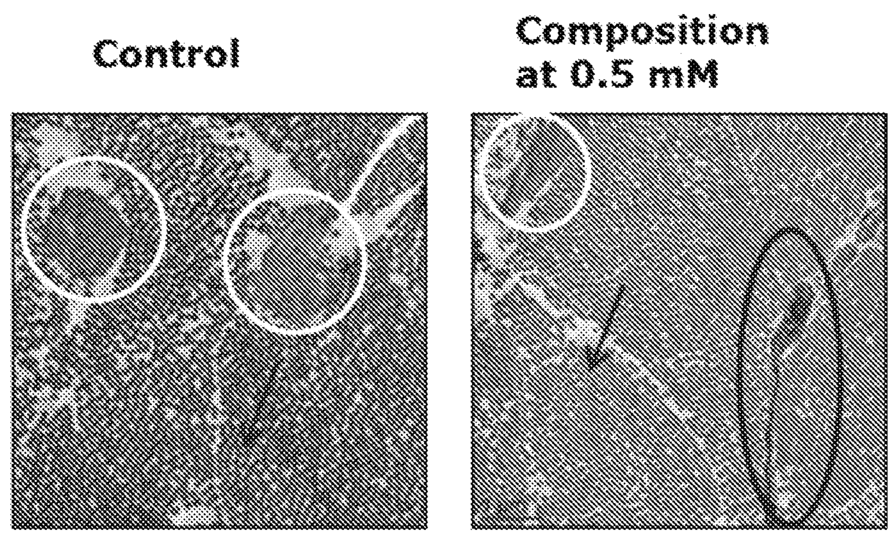

This is confirmed in FIG. 7, where telocytes are found to be numerous and look healthier in the skin treated with the composition. White rings focus on elastic fibers, black ring shows a telocyte, and arrows show collagen fibers.

Figure 8:
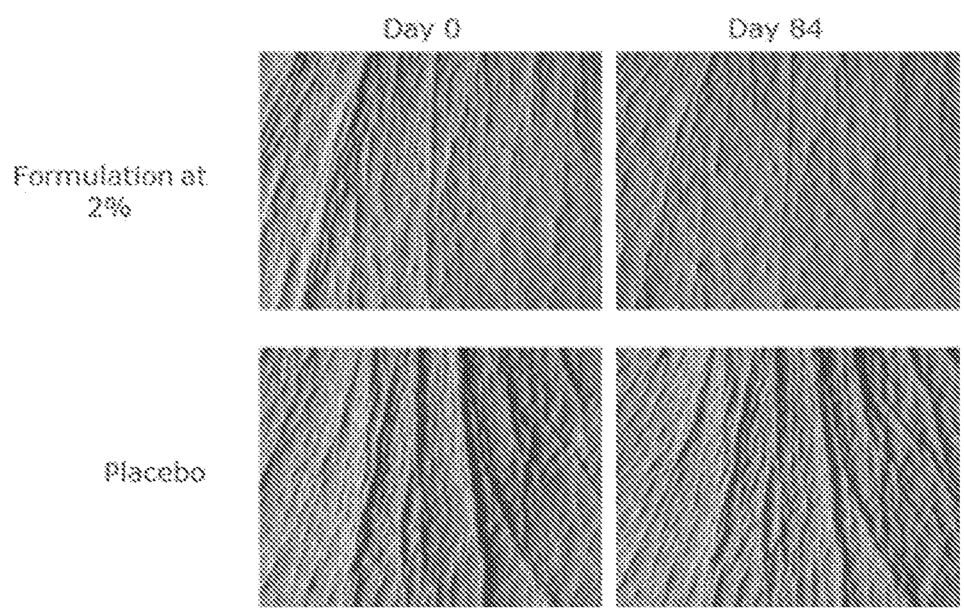

FIG. 8 shows the increase of the isotropy of the skin by use of a 2% formulation.

Figure 9:
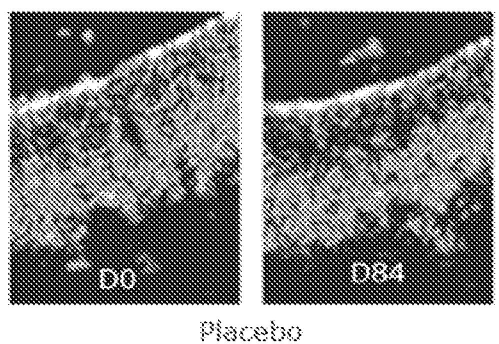
Figure 9:
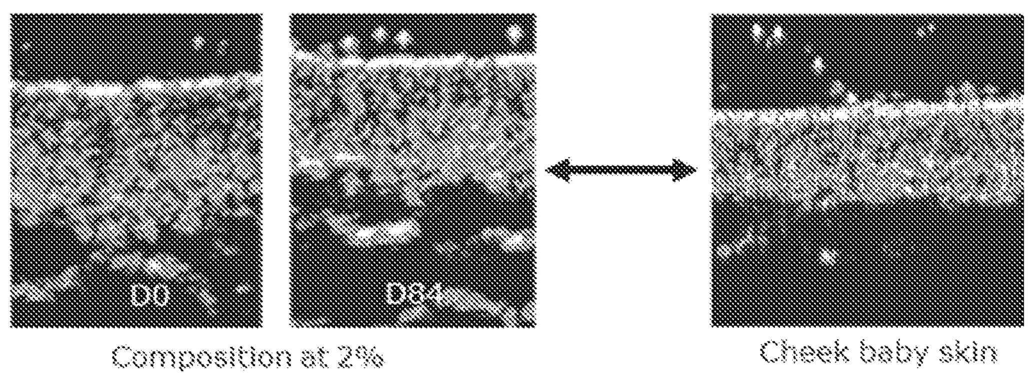

FIG. 9 shows the achievement of a compact dermis with more echogenic areas.

Figure 10:
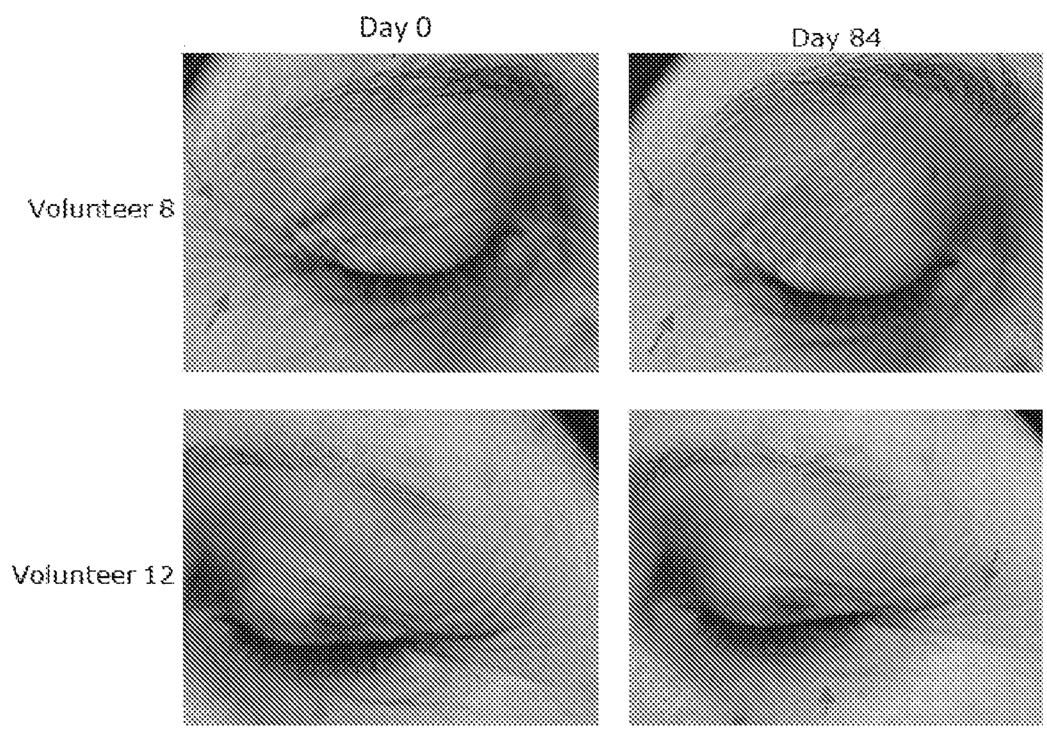

FIG. 10 shows the visible smoothing of the skin after treatment for 84 days.

Example 6

Effect of the Composition on Human Aged Skins (In Vivo Study)

Study protocol:

The clinical efficacy of the composition formulated in a cream at 2% was evaluated in a double blind test versus placebo under dermatological control by assessment of skin mechanical properties, skin isotropy, skin dermis echogenicity and silicone replicas after 14, 28, 56 and 84 days of application (respectively D14, D28, D56 and D84). Twenty four female volunteers aged between 47 to 65-years-old participated in the study, 50% of them being menopaused. The volunteers applied twice a day the placebo on one side of their face, and a cream containing 2% of the composition on the other side. Mechanical properties of the skin were evaluated on each side of their face after 2 weeks using Cutometer® tool. Cheek skin of a baby was also analyzed by ultrasound tool as a benchmark. The effect of the composition on skin dermis reorganization was evaluated by ultrasound tool. Skin isotropy was determined by PRIMOS 3D tool at D84. Skin isotropy is directly correlated with the quality and organization of the skin dermis. Some silicone replicas were made to visualize the skin surface, and full face pictures were taken with the Visia-CR device in standardized conditions, to illustrate the benefit for the volunteer. All raw data were statistically analyzed using a Student's t-test.

Results

Cutometer® Analysis

The composition at 2% gave in 14 days (D14) a significant improvement of the skin mechanical properties in comparison to placebo for all mechanical parameters studied: skin firmness, skin tonicity, skin viscoelasticity, and skin plasticity (table 8):

TABLE 8

Effect of composition formulated at 2% on skin mechanical properties (Cutometer ® measurements)

| % of increase of mechanical properties at D 14 in comparison to D 0 | % of improvement of placebo in comparison to D 0/ (p value) | % of improvement of the formulation 2% in comparison to D 0/ (p value) |
|---|---|---|
| Skin Firmness (R0 parameter) | 8%/ (p = 0.014) | 14%/ (p = 0.0001) |
| Skin tonicity | 7%/ (p: non-significant) | 16%/ (p = 0.002) |
| Skin viscoelasticity | 6%/ (p: non-significant) | 13%/ (p = 0.002) |
| Skin plasticity | 12%/ (p = 0.0001) | 22%/ (p = 0.0001) |

Skin Isotropy Analysis

Formulation at 2% increased the skin's isotropy: the rejuvenation of the skin matrix is clearly demonstrated on silicone replicas (FIG. 8).

Skin Echogenicity Analysis

The formulation at 2% visibly improved the skin density leading to a skin organization almost equivalent to baby skin. On the placebo side, a significant degradation of the skin matrix was observed (more black, decrease of the echogenic components), confirming the aging process progress. On the formulation applied side, a compact dermis was seen with more echogenic areas (FIG. 9).

The skin treated during 84 days with the formulation was visibly smoothed, as shown in FIG. 10 (see arrows). The formulation acted as a lifting agent, meaning that the dermis structure was better organized.

The invention claimed is:

1. A composition comprising 50 to 75 mmoles/kg N-acetyl-glucosamine-6-phosphate, 55 to 83 mmoles/kg glucuronic acid, and 33 to 66 mmoles/kg of a magnesium sulfate.

2. The composition according to claim 1, in which the three components are present in equimolar amounts.

3. A skin restoration product, comprising a composition according to claim 1.

4. The skin restoration product according to claim 3, in which the composition is present in an amount of from 0.005-5% by weight.

5. A method of restoring aged skin, comprising topically applying the product according to claim 3 to skin.

6. The composition according to claim 1, comprising 55 to 66 mmoles/kg N-acetyl-glucosamine-6-phosphate, 55 to 66 mmoles/kg glucuronic acid, and 55 to 66 mmoles/kg of a magnesium sulfate.

* * * * *